United States Patent
Klewinghaus et al.

(10) Patent No.: US 9,849,227 B2
(45) Date of Patent: Dec. 26, 2017

(54) ORGANIZER FOR RELEASABLY ACCOMMODATING COMPONENTS OF BLOOD TUBE SETS, AND METHODS FOR MANUFACTURING AND PREPARING IT

(75) Inventors: Jürgen Klewinghaus, Oberursel (DE); Michael Herrenbauer, Neu-Anspach (DE); Christine Nachbaur-Sturm, Eitorf (DE); Giovanni Di Rienzo, Crema (IT); Reinhold Reiter, Crema (IT)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1080 days.

(21) Appl. No.: 12/995,732

(22) PCT Filed: Jun. 4, 2009

(86) PCT No.: PCT/EP2009/004010
§ 371 (c)(1),
(2), (4) Date: Feb. 24, 2011

(87) PCT Pub. No.: WO2009/146913
PCT Pub. Date: Dec. 10, 2009

(65) Prior Publication Data
US 2011/0139652 A1 Jun. 16, 2011

(30) Foreign Application Priority Data
Jun. 5, 2008 (DE) .................. 10 2008 026 916

(51) Int. Cl.
*A61M 25/02* (2006.01)
*F16L 3/22* (2006.01)
(Continued)

(52) U.S. Cl.
CPC ............ *A61M 1/3621* (2013.01); *A61M 1/16* (2013.01); *A61M 1/34* (2013.01); *A61M 1/3413* (2013.01);
(Continued)

(58) Field of Classification Search
USPC ......... 248/74.2, 68.1; 24/336, 339; 604/179, 604/180; 128/DIG. 6, DIG. 26; 206/363,
(Continued)

(56) References Cited

U.S. PATENT DOCUMENTS 2,238,322 A 4/1941 Hodaly
2,873,820 A 2/1959 Rizzuto
(Continued)

FOREIGN PATENT DOCUMENTS

CN 1909937 2/2007
DE 199 59 965 A1 6/2000
(Continued)

OTHER PUBLICATIONS

International Search Report, PCT/EP2009/004010, mailed Aug. 1, 2010.
(Continued)

*Primary Examiner* — Jacob K Ackun
(74) *Attorney, Agent, or Firm* — Fish & Richardson P.C.

(57) ABSTRACT

The present invention relates to an organizer for releasably accommodating components of blood tube sets for different extracorporeal blood treatment options, in particular for dialysis methods, by means of a blood treatment apparatus, as well as methods for manufacturing and preparing an organizer of the invention.

17 Claims, 9 Drawing Sheets

(51) Int. Cl.
*A61M 1/36* (2006.01)
*A61M 1/16* (2006.01)
*A61M 1/34* (2006.01)

(52) U.S. Cl.
CPC ....... *A61M 1/3496* (2013.01); *A61M 2205/12* (2013.01); *A61M 2209/08* (2013.01)

(58) Field of Classification Search
USPC ....................................................... 206/370
See application file for complete search history.

(56) References Cited

U.S. PATENT DOCUMENTS

| | | | | |
|---|---|---|---|---|
| 3,491,971 | A * | 1/1970 | Fisher | 248/65 |
| 3,894,706 | A * | 7/1975 | Mizusawa | 248/68.1 |
| 4,069,968 | A * | 1/1978 | Herman | 494/1 |
| 4,406,042 | A | 9/1983 | McPhee | |
| 4,707,906 | A * | 11/1987 | Posey | 29/453 |
| 4,775,121 | A * | 10/1988 | Carty | 248/68.1 |
| 4,954,128 | A * | 9/1990 | Ford | A61M 1/308 |
| | | | | 604/6.05 |
| 4,999,885 | A | 3/1991 | Lee | |
| 5,085,326 | A * | 2/1992 | Russell et al. | 211/4 |
| 5,188,588 | A * | 2/1993 | Schoendorfer | A61M 1/30 |
| | | | | 604/6.07 |
| 5,200,090 | A * | 4/1993 | Ford | A61M 1/3441 |
| | | | | 210/104 |
| 5,226,892 | A * | 7/1993 | Boswell | 604/180 |
| 5,334,186 | A * | 8/1994 | Alexander | A61M 5/1418 |
| | | | | 128/DIG. 15 |
| 5,389,082 | A * | 2/1995 | Baugues et al. | 604/174 |
| 5,482,440 | A * | 1/1996 | Dennehey et al. | 417/63 |
| 5,613,655 | A * | 3/1997 | Marion | 248/68.1 |
| 5,628,908 | A * | 5/1997 | Kamen | A61M 1/28 |
| | | | | 210/180 |
| 5,870,805 | A * | 2/1999 | Kandler et al. | 24/459 |
| 6,298,525 | B1 | 10/2001 | Margo | |
| 6,349,170 | B1 | 2/2002 | Fressinet | |
| 6,382,569 | B1 * | 5/2002 | Schattner | F16L 3/04 |
| | | | | 248/220.41 |
| 6,458,104 | B2 * | 10/2002 | Gautsche | 604/179 |
| 6,533,116 | B1 * | 3/2003 | Riley | 206/363 |
| 6,629,005 | B2 | 9/2003 | Yoshinaga et al. | |
| 6,695,806 | B2 | 2/2004 | Gelfand et al. | |
| 7,223,338 | B2 * | 5/2007 | Duchamp et al. | 210/321.71 |
| 7,387,282 | B2 * | 6/2008 | Kovac | 248/74.4 |
| 7,457,506 | B1 * | 11/2008 | Osborne, II | 385/136 |
| 7,510,540 | B2 | 3/2009 | Valluzzi et al. | |
| 7,571,744 | B2 * | 8/2009 | Zia et al. | 138/106 |
| 7,621,009 | B2 * | 11/2009 | Elhabashy | A61B 50/20 |
| | | | | 248/68.1 |
| 7,731,132 | B2 * | 6/2010 | Raines, Jr. | 248/68.1 |
| 8,246,583 | B2 * | 8/2012 | Bierman | A61M 25/02 |
| | | | | 128/DIG. 26 |
| 2001/0048892 | A1 | 12/2001 | Bainbridge et al. | |
| 2002/0058896 | A1 | 5/2002 | Fressinet et al. | |
| 2003/0132352 | A1 | 7/2003 | Weaver | |
| 2004/0135039 | A1 * | 7/2004 | Reichert | F16L 3/1025 |
| | | | | 248/68.1 |
| 2005/0077436 | A1 * | 4/2005 | Nelson | F16L 3/223 |
| | | | | 248/68.1 |
| 2005/0165343 | A1 | 7/2005 | Valluzzi et al. | |
| 2006/0113432 | A1 * | 6/2006 | Driskell | A61M 39/08 |
| | | | | 248/68.1 |
| 2006/0282045 | A1 * | 12/2006 | Wilkinson et al. | 604/198 |
| 2007/0099053 | A1 | 5/2007 | Frey et al. | |
| 2007/0249983 | A1 | 10/2007 | Tonelli et al. | |
| 2013/0138044 | A1 * | 5/2013 | Schuman et al. | 604/174 |

FOREIGN PATENT DOCUMENTS

| | | |
|---|---|---|
| DE | 202 14 415 U1 | 4/2003 |
| DE | 10 2008 026 915.8 A1 | 12/2009 |
| EP | 0914048 B1 | 5/1999 |
| EP | 1159977 B1 | 12/2001 |
| EP | 1535635 A1 | 6/2005 |
| FR | 964745 A | 8/1950 |
| FR | 967017 A | 10/1950 |
| JP | 6395289 | 6/1988 |
| JP | 63095289 U | 6/1988 |
| JP | 04-093584 U | 8/1992 |
| JP | 3001188 | 8/1994 |
| JP | 3001561 | 8/1994 |
| JP | 60-69767 U | 5/1995 |
| JP | 3082021 | 11/2001 |
| JP | 3082021 U | 11/2001 |
| JP | 2003304928 A | 10/2003 |
| JP | 2004201904 A | 7/2004 |
| JP | 2005-059776 A | 3/2005 |
| JP | 2005312615 A | 11/2005 |
| JP | 2006043049 | 2/2006 |
| JP | 2007222306 A | 9/2007 |
| JP | 2007-283885 A | 11/2007 |
| JP | 04093584 | 6/2008 |
| JP | 2009514172 | 4/2009 |
| JP | 05317418 | 10/2013 |
| WO | 95/14172 A1 | 5/1995 |
| WO | 2007/091438 A1 | 8/2007 |
| WO | 2007/104350 A1 | 9/2007 |
| WO | 2009/146912 A1 | 12/2009 |

OTHER PUBLICATIONS

Japanese Search Report by Registered Searching Organization in Japanese Application No. 2011512023, dated Jun. 6, 2013, 9 pages (with English translation).

* cited by examiner

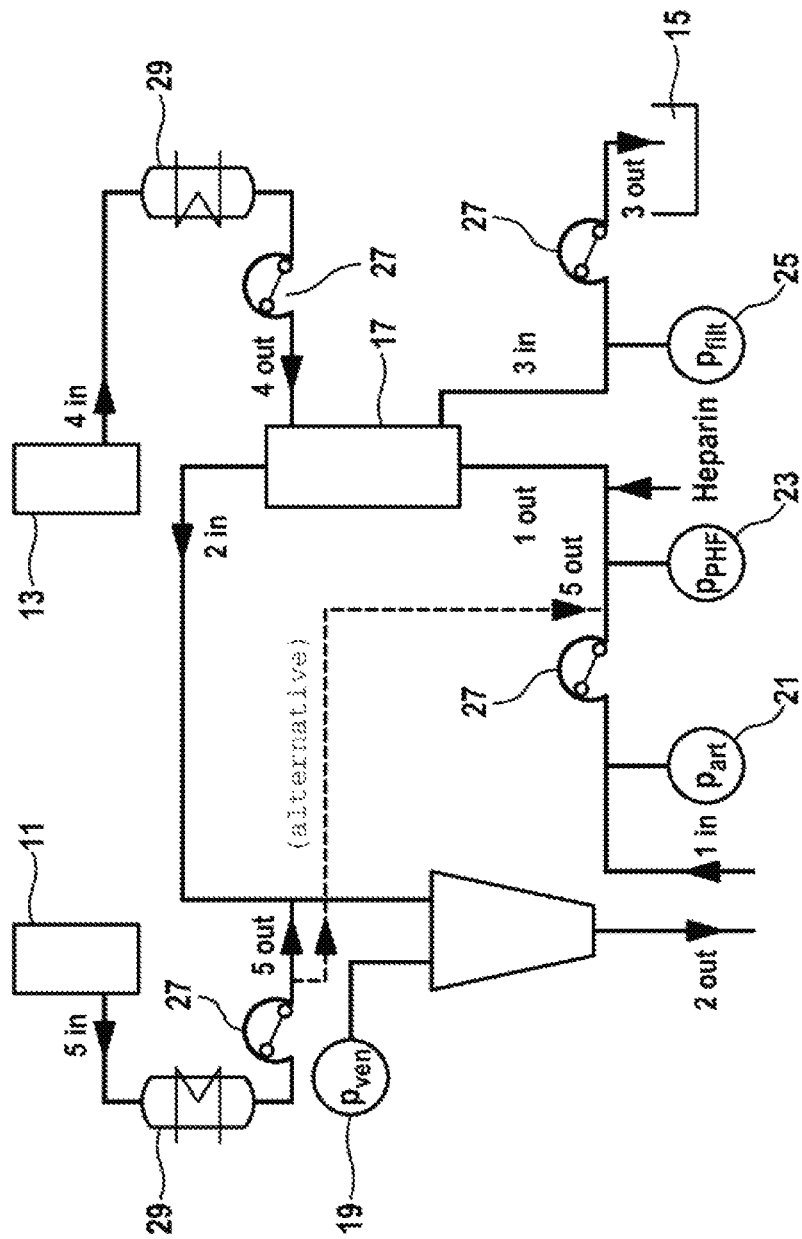

Fig. 3

| Short designation | Method | Used components | Removed components |
|---|---|---|---|
| CVVH | Hemofiltration | 2, 3, 5, 6 | 4 |
| CVVHD | Hemodialysis | 2, 3, 4, 6 | 5 |
| CVVHDF | Hemodiafiltration | 2, 3, 4, 5, 6 | --- |
| SCUF | Slow-Continuous Ultrafiltration | 2, 3, 6 | 4, 5 |
| MPS | Membrane Plasma Separation | 2, 3, 5, 6 | 4 |
| HV-CVVH | High-Volume Hemofiltration | 2, 3, 4, 5, 6 | --- |
| All named methods | Exchange of return line due to clotting | | 2 |
| All named methods | selectively with heparin or citrate/calcium anti-coagulation | 2, 3, 6 as well as 4 or 5 | 5 or 4, resp. |

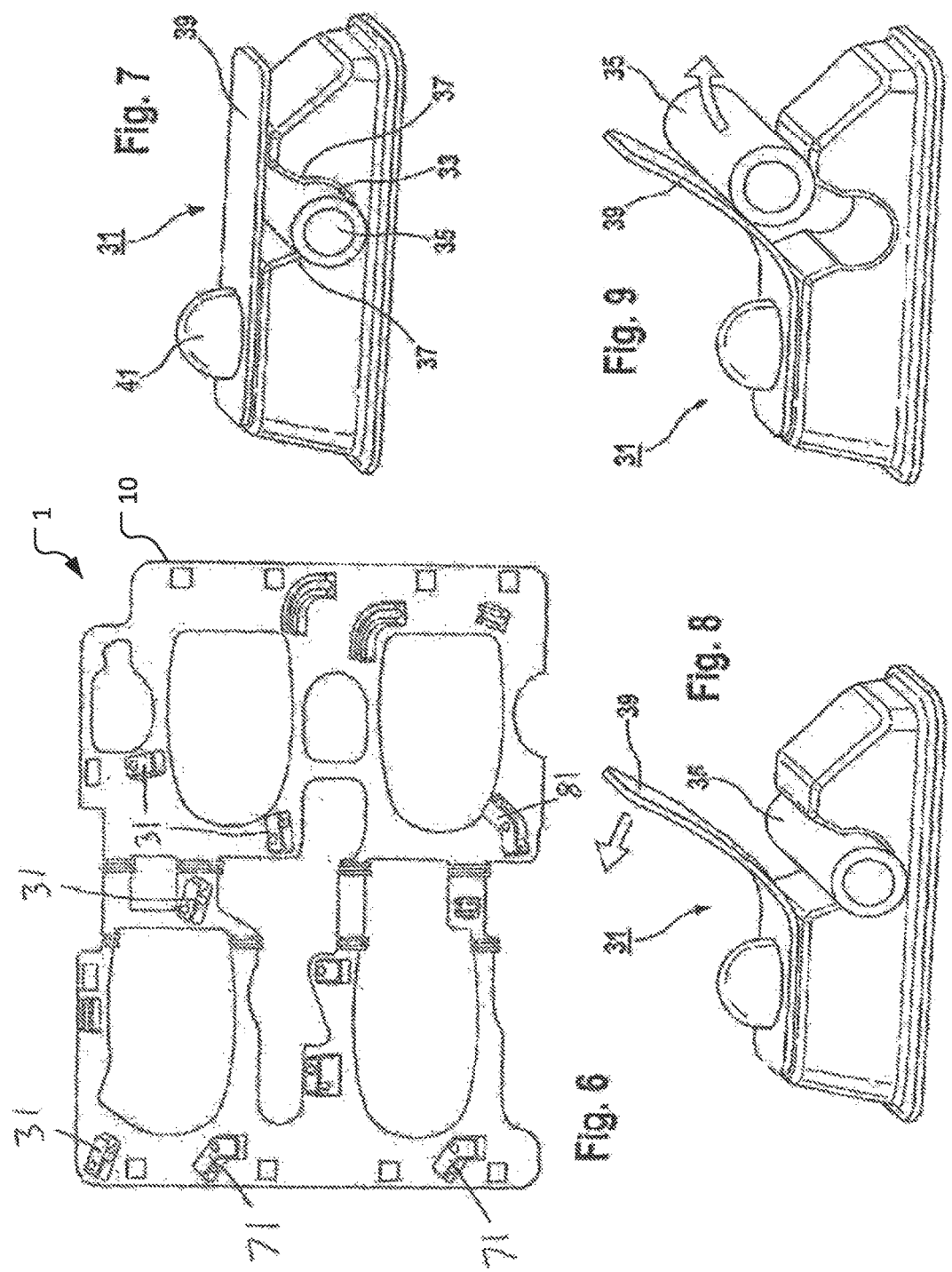

ORGANIZER FOR RELEASABLY ACCOMMODATING COMPONENTS OF BLOOD TUBE SETS, AND METHODS FOR MANUFACTURING AND PREPARING IT

CROSS REFERENCE TO RELATED APPLICATIONS

This is a 371 national phase application of PCT/EP2009/004010 filed Jun. 4, 2009, claiming priority to German Patent Application No. 10 2008 026 916.6 filed Jun. 5, 2008.

FIELD OF INVENTION

The present invention relates to an organizer. It furthermore relates to a method for manufacturing an organizer and a method for preparing the organizer.

BACKGROUND OF THE INVENTION

From practice, apparatus for the extracorporeal blood treatment, in particular for a dialysis treatment, are known which allow to selectively carry out different treatment methods or treatment options. For different treatment options, respective different volumes of blood tube sets (disposables) and associated components such as, e.g., tube connections and the like are necessary.

In the prior art, compositions of components for the formation of blood tubes are known from which blood tubes or treatment sets for different treatment options may be composed. Such compositions as the one known from EP 1 159 977 B1, for example, may be prepared on so-called "organizers" or "trays" in an orderly manner and in a manner suited for the coupling options furnished by the blood treatment apparatus being employed. Depending on the treatment option to be carried out, the blood tube set components may be connected correspondingly. The blood tube set components not required for the selected treatment option remain unused on the organizer.

An inherent drawback resides in the fact that the multiplicity of the components present on the organizer and their manifold interconnection options tend to confuse the hospital personnel, which regularly results in a wrong selection and connection of components, particularly under time pressure. In addition, the preparation of a ready-to-use blood tube set from the components present on the organizer for the selected treatment option requires experience and is moreover time-consuming, for several tube sets or tube lines must frequently be tracked conscientiously in order to avoid a wrong connection and confusion, while a large number of components having a similar appearance must be held in view.

SUMMARY OF THE INVENTION

It is an object of the present invention to specify another organizer or another tray, respectively. Thus, in accordance with the invention, an organizer for releasably accommodating components of blood tubes for different extracorporeal blood treatment options, in particular for dialysis methods, by means of a blood treatment apparatus such as, e.g., a dialysis apparatus, is proposed. The organizer is suited and prepared to receive components whereby at least one first blood tube set for a first blood treatment option or a second blood tube set for a second blood treatment option—that is independent of the first one—from among a group including several and at least two possible blood tube sets may be configured selectively during use of the organizer.

In the context of the invention, an "extracorporeal blood treatment option" is understood to be any blood treatment method for which the utilized blood treatment apparatus is suited. In the example of dialysis, these treatment options include i.a. hemofiltration, hemodialysis, hemodiafiltration, slow-continuous ultrafiltration, membrane plasma separation, and high-volume hemofiltration.

In the context of the invention, a "blood tube set" is understood to be a ready-to-use blood tube set (or a blood tube treatment set) having one or several components. Presently a blood tube set may be understood to be the sum total of all the components present on the organizer for a respective use in a particular treatment option.

The components of the organizer of the invention that are not necessary for a blood treatment option may be removed prior to the beginning of the treatment and may finally be discarded in a simple and secure manner. To this end, means for safely separating and removing unnecessary components or modular components may be provided. These means may include means for releasably fastening blood tube set portions or components on the organizer. The means may be of a design allowing to individually release some components without, at the same time, releasing other components that are required for the treatment. Thus, some components may be released and optionally discarded independently of others.

The invention is advantageously characterized by a high degree of attainable safety in connecting the treatment apparatus to the blood tube set, for a risk of confusion of components or a wrong connection in the preparation of a blood tube set for a selected one of the various possible treatment options is largely excluded thanks to the possibility of discarding components that are not required.

As a result, it is made possible that only the components actually needed have to be filled with solution during priming and rinsing, which advantageously contributes to economy of primers and solutions.

In an organizer which is suited and prepared for accommodating components for producing various blood tube sets that may be used separately of each other, the connection of these components to the treatment apparatus may be carried out in a simple and time-efficient manner. The arrangement of the single components relative to the treatment apparatus can be optimized with the aid of the organizer.

The components present on the organizer may moreover include different connection elements which may be connected to the treatment apparatus for the respective one treatment option for which they are intended, however not for other ones. This, too, serves to enhance safety in the utilization and connection of blood tube sets.

When using the organizer of the invention, the preparation of a blood tube set is not reserved to particularly experienced personnel any more but may also be carried out by less experienced collaborators.

The present invention furthermore allows to provide the organizer—at undiminished safety and rapid manipulation in comparison with the preparation of a single blood tube set—with all the components for different blood tube sets at the location of the treatment, whereby only one organizer can ensure that all the components for a blood tube set for every possible or desired blood treatment option are indeed present on site.

Another advantage of the organizer of the invention resides in the fact that its use can massively simplify stock keeping of components and blood tube sets. The multiplicity of the articles to be managed may be reduced to a single, universal article, namely, to the organizer itself. Although it is then regularly necessary to discard components of the organizer, the cost savings thus obtainable are nevertheless more important than the increased costs for discarding unneeded components in view of the simplified stock keeping.

Thus, in a preferred embodiment of the invention an integral organizer is proposed. In this point the organizer of the invention differs, for instance, from the organizer represented in FIG. 12 of EP 0 914 048 B1. The latter is only suited for the orderly arrangement of a multiplicity of components such as tubes for one or several blood tube sets. Owing to its frame-type structure with a top or bottom half-frame it is, however, hardly possible under practical conditions to remove single tube portions without other tube portions equally coming off the organizer or getting into disarray. This drawback is remedied by the integral configuration of the organizer of the invention in this embodiment of the invention.

In the context of the invention, an "integral" configuration is also understood to be one wherein further structural elements are added to the main body of the organizer following, e.g., a casting or injection molding process for its manufacture. In connection with "integral" it is solely of relevance in the framework of the invention that the organizer of this embodiment of the invention does not have to be opened—unlike the prior-art frame structure described above—in order to remove unneeded blood tube components. Selecting the components required for an intended blood treatment option and discarding the remaining components is thus advantageously also possible on minimum space and without the risk of causing disarray within the group of the blood tube sets or components.

By means of the organizer of the invention it is advantageously possible to specifically remove particular components, tube sections, or entire tube sets from the organizer without inadvertently also releasing further components. An inadvertent release of components is hereby prevented.

The same advantage as in the integral configuration may also be achieved if the organizer is configured to be equipped with blood tube components from an exposed side in the sense of a freely accessible side. This, too, is meant to be understood as "integral."

In a further preferred embodiment, the organizer comprises at least one fastening means for "fastening element") for releasably fastening blood tube components, i.e., one or several blood tube sets. Inadvertent release of tube sections or the like from the organizer may advantageously be avoided through deliberate use of the fastening means. Situations easily giving rise to errors may thus be avoided. The fastening means moreover contributes to purposely releasing particular tube sections without inadvertently also separating other components from the organizer.

In a preferred embodiment, a particularly simple and cost-efficient configuration of the fastening means of the organizer of the invention comprises at least one receiving portion for releasably accommodating at least one component on the organizer, wherein it may be configured to have a depression for receiving the component along a portion of a periphery of the component. In this embodiment, the fastening means furthermore comprises a tab or flap whereby the component may releasably be secured in the receiving portion. This may in particular include closing the depression of the receiving portion, and in particular closing it in a reversible manner.

This configuration of the fastening means includes improvements in comparison with fastening means that are known from the prior art, such as those known, e.g., in the form of a clip from U.S. Pat. No. 6,298,525 B1. Such clips or known fastening means in general exhibit the drawback that the tension they exert on the components of the blood tube set for their fixation eases off in the course of time due to material relaxations. Such relaxations may occur, e.g., owing to the duration or circumstances of storage, or even sterilization of the fastening means or of the organizer carrying the fastening means. As a result of this relaxation, components may inadvertently come free from the fixation, which may in turn lead to complex situations easily giving rise to errors, particularly in the presence of a multiplicity of components for different treatment options.

The provision of the tab whereby the component or several components in the receiving portion or in several receiving portions are releasably secured, forcibly necessitates a consciously performed operation in order to release the component(s). This operation may consist in folding up or pivoting away the tab or flap, etc. An inadvertent release of the tube section such as, e.g., from the above-described clip or from a groove-type slit that is also known from the prior art as disclosed, i.a., in US 2003/0132352 A1, can be avoided in accordance with the invention. At least the likelihood of its occurrence is notably reduced.

In particular, the receiving portion may be configured to include a depression wherein portions of the component may be accommodated, in particular along a peripheral portion thereof. The tab may be provided in order to close the depression along its periphery, i.e., in order to complete its periphery in a positive and/or frictional manner.

As provided by a further preferred embodiment, the tab may have an elastic configuration. This allows simple folding or bending up of the tab in order to remove the component from the associated receiving portion. Such an elastic configuration ensures that the component will remain in the receiving portion. Inadvertent opening of the tab, which might furthermore go unnoticed, is advantageously prevented owing to the elasticity of the tab and the accompanying resetting effect.

In another further preferred embodiment, the fastening means comprises at least one portion that is suited to facilitate raising the tab by a user's finger. To this end, the portion may be inclined to thus allow the finger to reach around between tab and organizer. The same advantageous effect may be obtained or enhanced by the provision of a protruding extension of the tab, which in turn may easily be grasped by the finger. The inclination of the portion may in particular relate to a plane of main extension of the organizer. The positive or negative inclination of the portion relative to the plane of main extension of the organizer may in a preferred manner assume an angle of 20-80°, in a particularly preferred manner of 30-70°, in an especially preferred manner of 40-60°, as well as any intermediate values of these ranges.

In a further preferred embodiment, the tab of the fastening means of the organizer may moreover be adapted to pivot. Here an optional elastic configuration of the tab may in turn bring about an automatic pivoting return movement into a secured position while achieving the advantages discussed above. Latching of the tab, for instance in a portion of the fastening means, may furthermore be provided so as to secure the tab against an inadvertent pivoting movement from the secured position.

In another further preferred embodiment, any one organizer in accordance with the above description comprises components for configuring at least one blood tube set. In an organizer thus equipped, the dimensions of at least one fastening means and at least one blood tube set component may be harmonized such that the blood tube set component may be clamped in the fastening means—in addition or as an alternative to other securing and fastening means. This also advantageously prevents an inadvertent and undesired release of components from the organizer.

The organizer of every embodiment may be made of, or comprise, polystyrene. The organizer may be produced, i.a., by thermoforming.

In a further preferred embodiment of the organizer according to the invention, a tube inserted therein is retained only or mainly only by form closure. In such an embodiment, the tube is only elastically compressed when being inserted and/or removed, and also in these cases only for a short time, namely while passing the bottleneck in order to be placed into a channel provided for its accommodation. Once inserted, the tube in this embodiment is advantageously being not or only inessentially elastically deformed. Such an embodiment has the further advantage that during sterilization (e.g., steam sterilization) of the organizer with inserted elements no plastic deformation or only inessential plastic deformation of the tube due to relaxation (tensions declining with time during constant deformation) occur in the area of the clip.

The object of the invention is furthermore achieved through a method for manufacturing an organizer, in particular one according to the preceding discussion. In addition, the object of the invention is achieved through a method for preparing an organizer. As the advantages discussed in the foregoing in connection with the organizer of the invention may be attained undiminished through the methods of the invention, explicit reference is here made to their discussion given above so as to avoid repetitions.

The organizer of the invention may allow one to replace parts or components of the blood tube set or the entire blood tube set with new disposables during an interruption of the blood treatment. Such a replacement of parts may become necessary, e.g., owing to coagulation of blood in the filter. The use of the organizer appended to the machine would be continued in this case.

BRIEF DESCRIPTION OF THE DRAWINGS

The present invention shall be described exemplarily in the following by referring to the appended drawings in which same reference symbols designate identical elements, and wherein:

FIG. 2 shows a possible block diagram for a hemodiafiltration.

FIG. 3 represents the respective blood tube sets used for a treatment option and possibly removed tube set components in the form of a table.

FIG. 6 shows a top view of an organizer of the invention which is not equipped with blood tube components.

FIG. 7 shows a fastening element having a receiving portion for releasably accommodating a portion of a blood tube in a first embodiment thereof.

FIG. 8 shows the fastening element of FIG. 7.

FIG. 9 shows the fastening element of FIGS. 7 and 8.

DETAILED DESCRIPTION OF THE DRAWINGS

Figure 1:
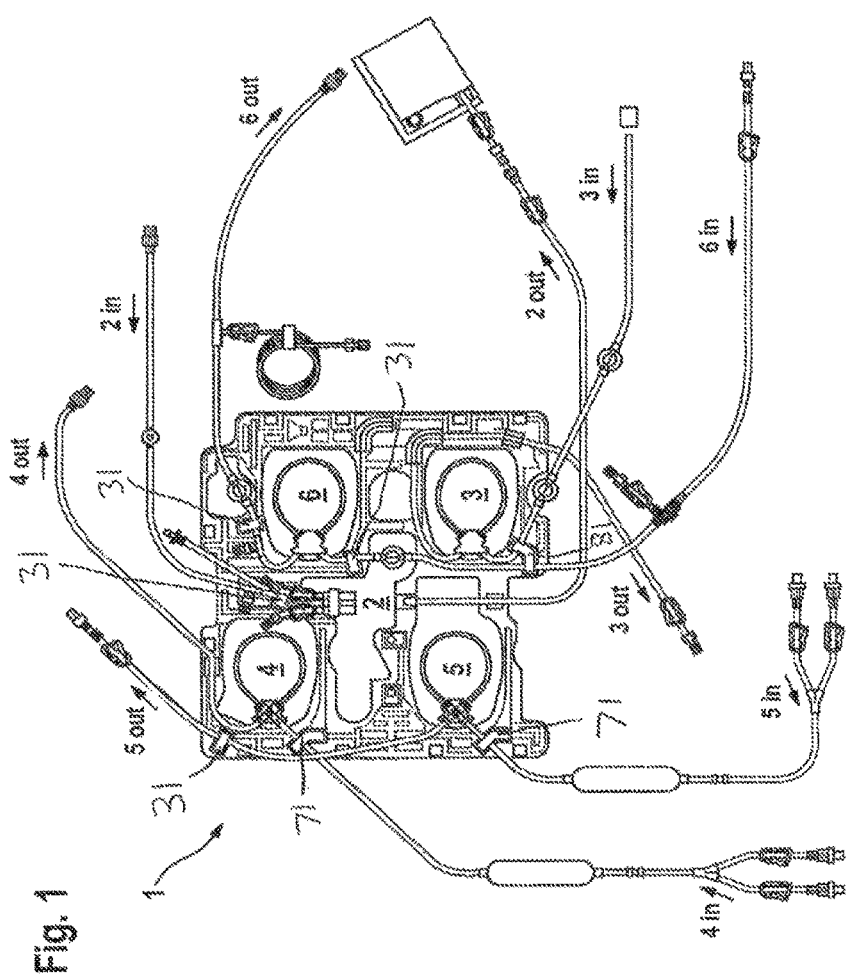
FIG. 1 shows an exemplary organizer of the invention.

FIG. 1 is a schematically simplified view of an exemplarily equipped organizer of the invention 1, which is equipped with a return line 2 from a filter (not shown) to the patient, a filtrate line 3 from the filter to a filtrate bag (not shown), a dialysate line 4 for dialyzing liquid or substitution liquid from a solution bag (not shown) to the filter or connection part, a substituate line 5 for substitution liquid from the solution bag to the connection part in a supply line 6 from the patient to the filter or to the return line 2.

The return line 2 here includes a filter connector 2 in as well as a patient connector 2out with rinsing bag. The filtrate line 3 includes a filter connector 3 in and a connector 3out for the filtrate bag. The dialysate line 4 includes a connector 4 in for the solution bag and a filter connector 4out or for a connection part in the supply or return line. The substituate line 5 includes a connector 5 in for the solution bag as well as a connector 5out for the connection part in the supply or return line. The supply line 6 from the patient to the filter includes a patient connector 6 in as well as a filter connector 6out.

The organizer 1 may include hanging eyelets X, Y, which may be realized in the form of recesses as shown in FIG. 1 or may have some other configuration. By means of these, the organizer 1 may be suspended on two hooks or buttons provided at the treatment apparatus (not shown in FIG. 1). During the treatment, the organizer 1 together with components remaining on it stays on the treatment apparatus. The fastening means of the organizer described further below serve, i.a., for guiding or retaining the tubes or components during the treatment, so that it is not necessary to provide any machine-side mounts for this purpose. The organizer 1 is only taken off the treatment apparatus once the treatment is completed. The organizer 1 preferably is configured such that a previous removal of the organizer (without components) from the treatment apparatus is not possible or is at least not possible by mistake.

FIG. 2 shows a possible block diagram for a hemodiafiltration with all the components that are also shown in FIG. 1. FIG. 2 furthermore shows a substituate bag 11, a dialysate bag 13, a filtrate bag 15, as well as a dialysis apparatus 17. FIG. 2 moreover represents pressure sensors 19, 21, 23 and 25 as well as additional further components for extracorporeal blood circuits that are known to the skilled person, such as pumping segments 27 and heating bag 29.

FIG. 3 represents respective components and optionally removed components for a particular method or for a particular treatment option of the treatment apparatus used in the form of a table.

Figure 4:
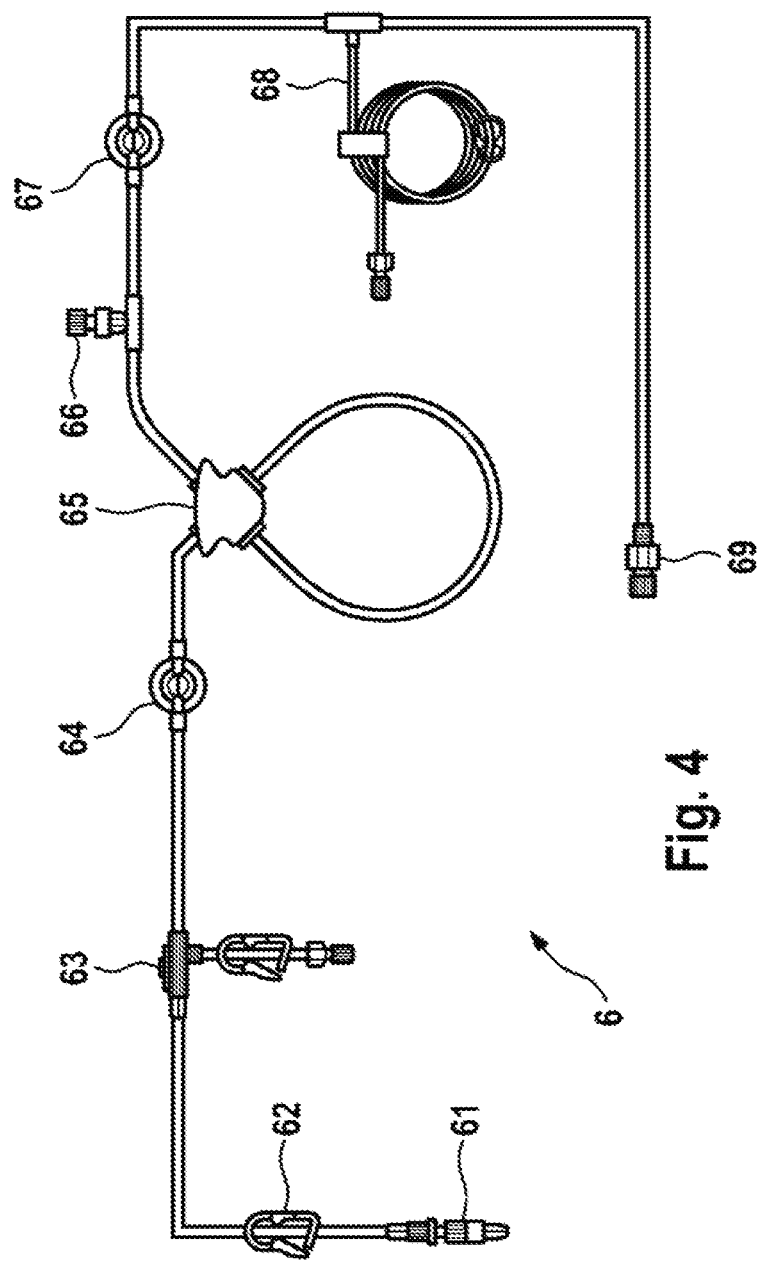
FIG. 4 shows a supply line from the patient to the filter, which is also shown in FIG. 1.

FIG. 4 shows the supply line 6 from the patient to the filter, which is also known from FIG. 1. The supply line 6 comprises a patient connector 61 having a cap, a tube clamp 62, an infusion port 63, a pressure tap 64, a pumping segment 65 for a roller pump, a connection part 66 having a check valve for the exchange of liquid, a pressure tap 67 for measuring a pre-filter pressure, a connection line 68 for heparin administration or some other anti-coagulation, as well as a filter port 69 having a cap.

Figure 5:
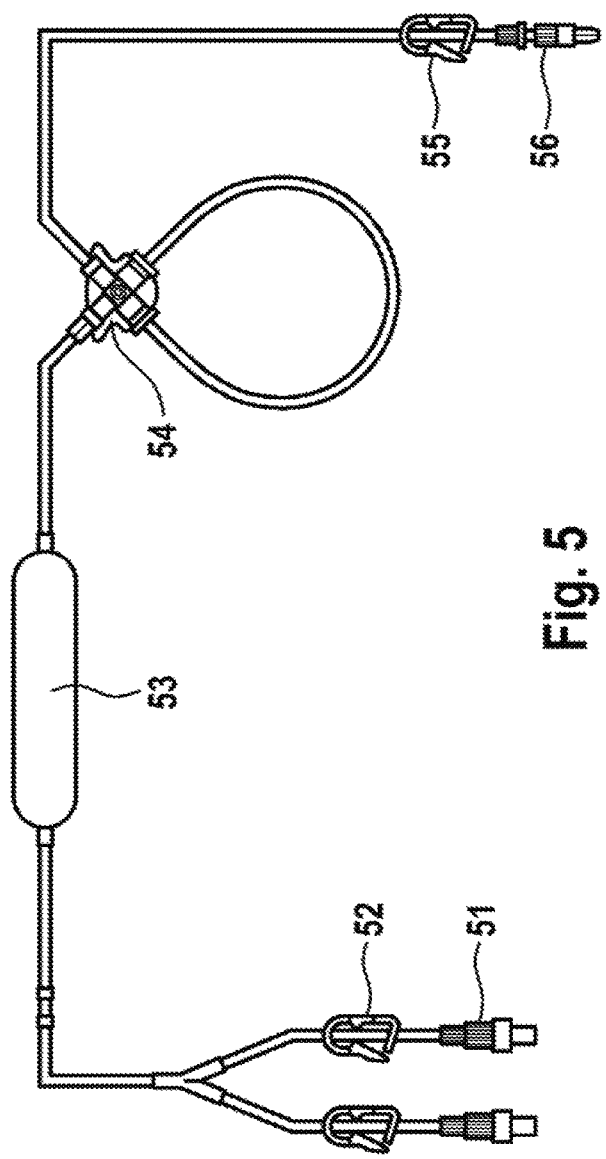
FIG. 5 shows a substituate line which is also shown in FIG. 1.

FIG. 5 shows a substitute line 5 which is also shown in FIG. 1. The line 5 comprises a connector 51 for a solution bag having a cap, a tube clamp 52, a heating bag 53, a pumping segment 54, a tube clamp 55, as well as a connector 56 for a line connection part having a cap.

FIG. 6 shows an overview or top view of an organizer 1 with a main body 10 that is not equipped with blood tube components.

FIG. 7 shows a first embodiment of a fastening element 31 having a receiving portion 33 for releasably accommodating one portion of a blood tube 35, with the receiving portion 33 comprising inclined surfaces 37 for a simplified reception of the tube section 35 in the receiving portion 33. FIG. 7 furthermore shows a tab 39 that is affixed to the fastening element 31 by means of a fixation means 41. As is discernible in FIG. 8, the tab 39 is configured to be elastic and may be raised or bent up elastically for removing the tube 35 in accordance with the representation in FIG. 9. By virtue of its predetermined elasticity, it prevents an inadvertent release of the tube 35 from the receiving portion 33.

The fixation means 41 of the embodiments for fastening the tab of FIGS. 7 through 9 preferably is a weld spot. In this case, the tab is connected to the fastening means while being secured against rotation. It is, however, also possible give to the fixation means 41a rotatable configuration, for instance with the aid of a rivet and/or a rotatable snap connection. In this case the tab may be opened by rotation, so that the tube segment may be removed easily and without any significant exertion of force.

Figure 10:
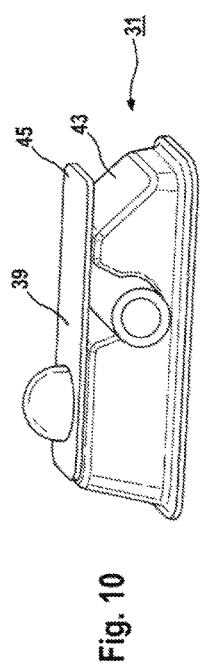
FIG. 10 shows the fastening element known from FIGS. 7, 8, and 9.

FIG. 10 shows the fastening element 31 known from FIGS. 7, 8, and 9, comprising an inclined portion 43 whereby raising of the tab by the user is favored or facilitated, respectively. This is furthermore aided by a protruding rim or protrusion 45 of the tab 39.

Figure 11:
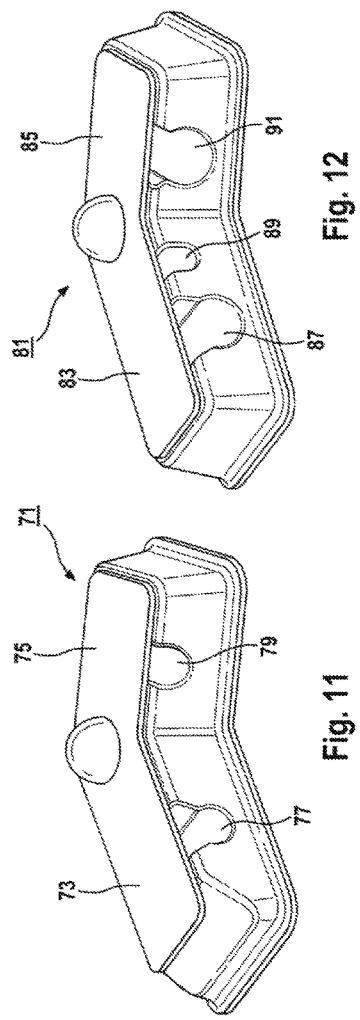
FIG. 11 shows a fastening element in a second embodiment thereof.

FIG. 11 shows a fastening element 71 in a second embodiment. The fastening element 71 comprises two tabs 73 and 75 each closing a respective receiving portion 77 and 79 in the same manner as was described by referring to FIGS. 7 through 10.

Figure 12:
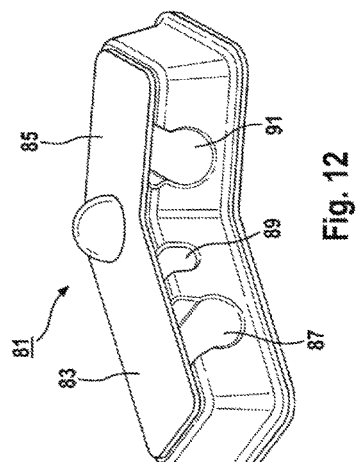
FIG. 12 shows a third embodiment of the fastening element for an organizer having two tabs for securing three receiving portions.

FIG. 12 shows a fastening element 81 which comprises two tabs 83 and 85 for closing three receiving portions 87, 89, and 91. In each embodiment, the receiving portions may have respective same or different geometrical extensions.

Figure 13:
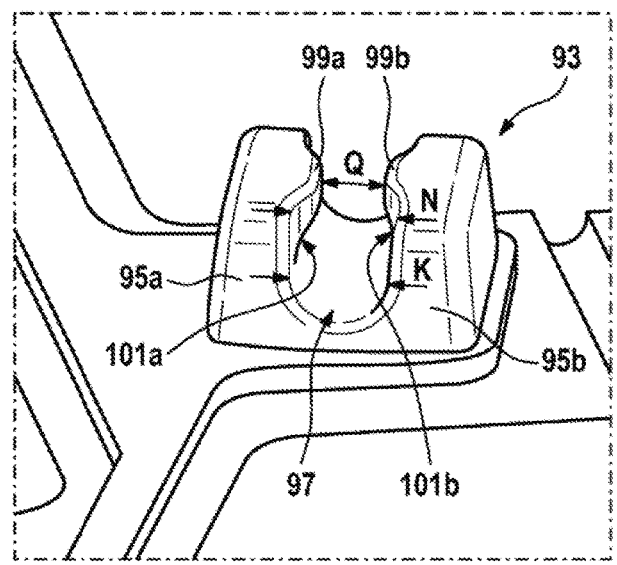
FIG. 13 shows a fourth embodiment of the fastening element according to the invention in a perspective view.

FIG. 13 shows a fastening element 93 according to the invention according to a fourth embodiment in a perspective view. The fastening element 93 is designed or embodied as a clip. The fastening element 93 comprises two legs 95a and 95b, the legs 95a and 95b each laterally confining one channel 97 (in FIG. 13) which is open to the top and to its front and back sides. The channel 97 thus being designed or embodied partly open or half-open serves for accommodating or hosting a tube segment not shown in FIG. 13.

The legs 95a and 95b each have a protrusion or reinforcement, respectively, 99a and 99b, respectively, showing into the direction of the top opening having the width Q of the channel 97. By means of the reinforcements 99a and 99b, a clamping effect on a tube segment (not shown) inserted into the fastening element 93 may be achieved. It is also possible to provide the protrusions or reinforcements along the channel 97 by turns or alternately ("staggered" or "offset") on or at the one side or the other side of the channel 97 such that no protrusions or reinforcements facing each other occur or protrusions or reinforcements do not oppose each other across the channel 97. Thereby, a particularly easy inserting of the tube is enabled. This advantageously allows for the tube segment to be detachably fixed in the fastening element 93 in a simple yet safe manner.

The arrangement or construction or design of the fastening element 93 does not have to feature the arrangement or construction or design of the channel cross-section with indentations 101a and 101b recognizable from FIGS. 13 to 16 for the tube segment to be fixed in a simple yet safe manner. Indeed, the indentations 101a and 101b which determine the width Q of an opening, which is less than a width K of a channel segment into which the tube segment is placed within the fastening element 93, offer an again increased security that the tube segment is not inadvertently detached from the fastening element 93. Even so, it is not necessary according to the invention to provide such indentations.

Also encompassed by the invention is providing only one indentation, e.g., 101a or 101b, at or on only one leg 95a or 95b. Likewise encompassed by the invention is that only one of the legs 95a or 95b—or both legs 95a and 95b—comprise more than only one protrusion or reinforcement, respectively—like, for example, the reinforcement 99a or 99b. Also, the legs 95a or 95b may comprise different numbers of protrusions or reinforcements (e.g., 0 and 1, 1 and 2, 0 and 2, etc.).

Figure 14:
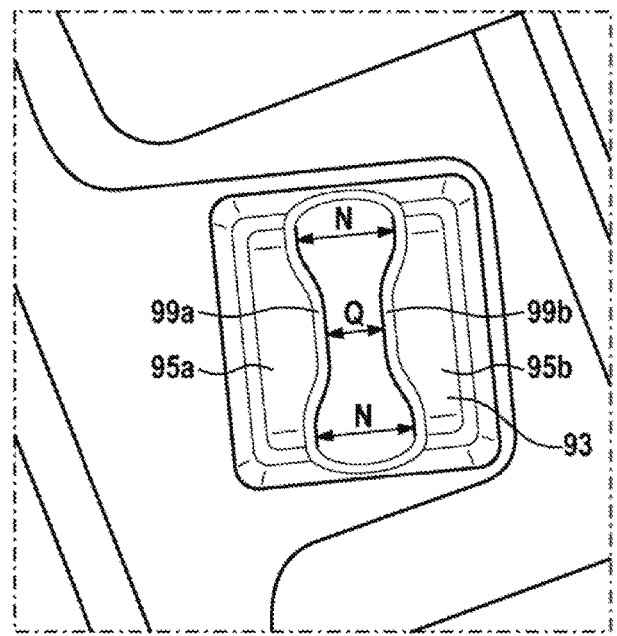
FIG. 14 shows the fastening element of FIG. 13 in a plan view.

FIG. 14 shows the fastening element 93 of FIG. 13 in a plan view. It is easily recognizable that due to the reinforcements 99a and 99b in the plan view the fastening element 93 has an hour glass-like shape. The channel 97 has this shape in longitudinal sections in an upper area thereof, as is recognizable from, e.g., FIG. 15 and, in particular, FIG. 16. There, width Q is less than a width N. In contrast, in a lower area of the fastening element 93 (see, e.g., FIG. 16), a longitudinal section may assume a rectangular shape again. It is noted that the protrusions or reinforcements 99a and 99b are only exemplarily arranged in a middle longitudinal section of the channel 97 as in FIGS. 13 to 16, which leads to the typical hour glass-shape of some longitudinal sections. The protrusions or reinforcements 99a and 99b may of course also be provided in an area near one or both front sides of the channel 97 and/or at a yet again different location.

Figure 15:
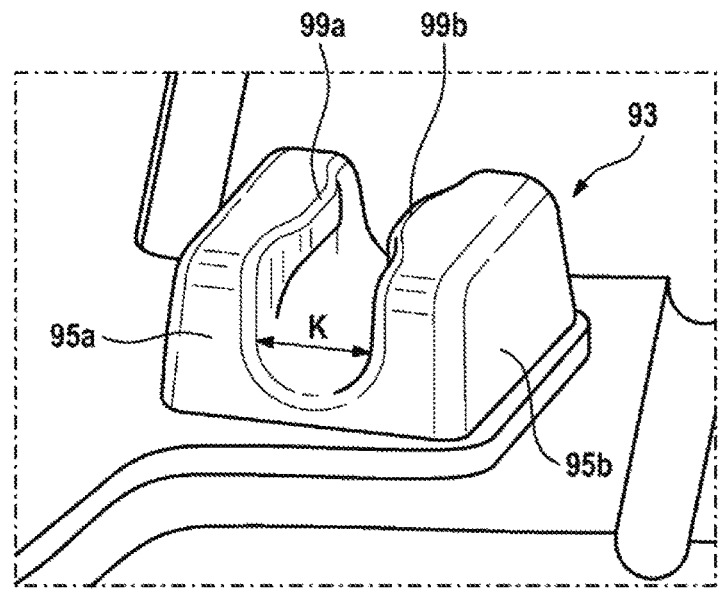
FIG. 15 shows the fastening element of FIGS. 13 and 14 in a further perspective view.
Figure 16:
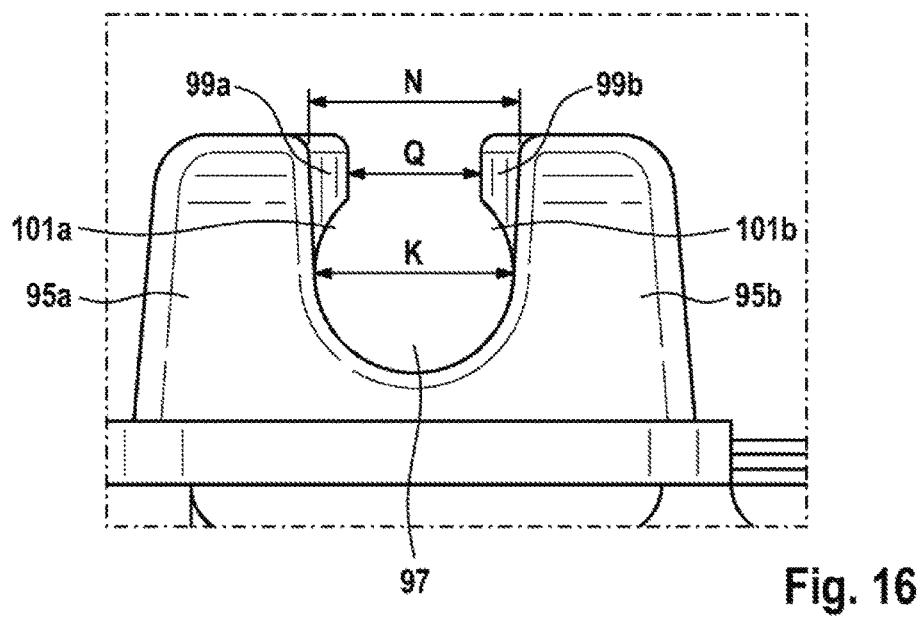
FIG. 16 shows the fastening element of FIGS. 13 to 15 in a lateral or side view.

FIG. 15 shows the fastening element 93 of FIGS. 13 and 14 in a further perspective view, and FIG. 16 shows the fastening element 93 of FIGS. 13 to 15 in a lateral or side view.

In accordance with the invention it is possible to either dispose of the organizer of the invention after the treatment, together with parts of the disposables or components, or in turn to supply the organizer without disposables to recycling (material recycling). It is, however, also possible to supply the organizer to a reuse (repeated use). To this end it may be advantageous if the fastening means (e.g., the tab 39 or even the entire fastening element 31) can be removed from the organizer and disposed of together with the disposable(s). As a possible embodiment of the fastening means, e.g., latching by means of a snap connection is conceivable. For a reuse of the organizer, the tab/fastening means would then be replaced with a new tab/fastening means.

The invention claimed is:

1. An organizer for a blood treatment apparatus, comprising:
   a main body;
   a plurality of blood tubes to be used for a plurality of blood treatments selected from the group consisting of hemofiltration, hemodialysis, hemodiafiltration, slow-continuous ultrafiltration, membrane plasma separation, and high-volume hemofiltration; and
   a fastening element for releasably fastening portions of the blood tubes on the organizer, the fastening element comprising:
      a first receiving portion including a first depression for releasably accommodating a portion of a first one of the blood tubes;
      a first tab that closes a periphery of the first depression, wherein the first tab has an elastic configuration that allows the first tab to be bent in order to remove the portion of the first one of the blood tubes from the first receiving portion;
      a second receiving portion including a second depression for releasably accommodating a portion of a second one of the blood tubes; and
      a second tab that closes a periphery of the second depression, wherein the second tab has an elastic configuration that allows the second tab to be bent in order to remove the portion of the second one of the blood tubes from the second receiving portion,
      wherein a fixation means positioned between the first tab and the second tab connects the first tab and the second tab to other portions of the fastening element.

2. The organizer according to claim 1, wherein the organizer has an integral configuration.

3. The organizer according to claim 1, wherein at least one of the first tab and the second tab includes a portion that protrudes from other portions of the fastening element to facilitate raising of the tab via a user's finger.

4. The organizer according to claim 3, wherein at least one of the first receiving portion and the second receiving portion comprises inclined surfaces.

5. The organizer according to claim 1, wherein at least one of the first tab and the second tab is adapted to pivot in relation to other portions of the fastening element.

6. The organizer according to claim 1, wherein the fastening element is a first fastening element, and wherein the organizer further comprises one or more additional fastening elements with the same structure as the first fastening element.

7. The organizer according to claim 1, wherein the fastening element further comprises a third receiving portion including a third depression for releasably accommodating a portion of a third one of the blood tubes, and wherein the first tab closes a periphery of the third depression.

8. The organizer according to claim 7, wherein the first depression and the third depression have differing sizes.

9. The organizer of claim 1, wherein the plurality of blood treatments are selected from the group consisting of hemofiltration, hemodialysis, hemodiafiltration, slow-continuous ultrafiltration, membrane plasma separation, and high-volume hemofiltration.

10. The organizer according to claim 1, wherein the fixation means comprises a weld spot.

11. The organizer of claim 1, wherein the fixation means is a rotatable connection.

12. The organizer of claim 1, wherein the blood tubes that are not used during the selected one of the plurality of blood treatments are releasable from the organizer.

13. The organizer of claim 1, wherein each of the plurality of blood tubes includes a connection element configured to connect the respective blood tube to the blood treatment apparatus for only a specified extracorporeal blood treatment option.

14. The organizer of claim 1, wherein the plurality of blood tubes comprises a return line, a filtrate line, a substituate line, and a supply line.

15. The organizer of claim 1, wherein the plurality of blood tubes comprises a return line, a filtrate line, a dialysate line, and a supply line.

16. The organizer of claim 1, wherein the plurality of blood tubes comprises a return line, a filtrate line, a dialysate line, a substituate line, and a supply line.

17. The organizer of claim 1, wherein the plurality of blood tubes comprises a return line, a filtrate line, and a supply line.

* * * * *

UNITED STATES PATENT AND TRADEMARK OFFICE
CERTIFICATE OF CORRECTION

| | |
|---|---|
| PATENT NO. | : 9,849,227 B2 |
| APPLICATION NO. | : 12/995732 |
| DATED | : December 26, 2017 |
| INVENTOR(S) | : Jürgen Klewinghaus et al. |

Page 1 of 1

It is certified that error appears in the above-identified patent and that said Letters Patent is hereby corrected as shown below:

On the Title Page

Column 1, (Inventors), Line 5, delete "Crema (IT);" and insert --Hemel Hempstead (GB);--.

Signed and Sealed this
Tenth Day of April, 2018

Andrei Iancu
*Director of the United States Patent and Trademark Office*